US008496916B2

(12) United States Patent
Harichian et al.

(10) Patent No.: US 8,496,916 B2
(45) Date of Patent: Jul. 30, 2013

(54) SUNSCREEN COMPOSITION WITH POLYHYDROXY QUATERNARY AMMONIUM SALTS

(75) Inventors: Bijan Harichian, Trumbull, CT (US); Van Au, Trumbull, CT (US); Neil Patrick Randle, Trumbull, CT (US); Stephen Roy Barrow, Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/477,564

(22) Filed: May 22, 2012

(65) Prior Publication Data

US 2013/0129644 A1 May 23, 2013

Related U.S. Application Data

(60) Provisional application No. 61/562,473, filed on Nov. 22, 2011.

(51) Int. Cl.
*A61K 8/00* (2006.01)

(52) U.S. Cl.
USPC .......................................... 424/59

(58) Field of Classification Search
None
See application file for complete search history.

(56) References Cited

U.S. PATENT DOCUMENTS

| | | | |
|---|---|---|---|
| 5,089,578 A | 2/1992 | Valint et al. | |
| 5,135,747 A | 8/1992 | Faryniarz | |
| 5,686,082 A | 11/1997 | N'Guyen | |
| 5,833,999 A | 11/1998 | Trinh | |
| 5,849,310 A | 12/1998 | Trinh et al. | |
| 5,891,452 A | 4/1999 | Sebillote-Arnaud et al. | |
| 5,952,395 A | 9/1999 | Lorant | |
| 5,961,961 A | 10/1999 | Dobkowski et al. | |
| 6,086,903 A | 7/2000 | Trinh et al. | |
| 6,100,233 A | 8/2000 | Sivik | |
| 6,869,977 B1 | 3/2005 | O'Lenick, Jr. et al. | |
| 7,175,834 B2 * | 2/2007 | Aust et al. | 424/59 |
| 7,659,233 B2 | 2/2010 | Hurley et al. | |
| 8,124,063 B2 | 2/2012 | Harichian et al. | |
| 8,173,108 B2 | 5/2012 | Misso et al. | |
| 8,206,691 B2 * | 6/2012 | Polonka et al. | 424/60 |
| 2012/0259011 A1 * | 10/2012 | Misso | 514/547 |

FOREIGN PATENT DOCUMENTS

| | | |
|---|---|---|
| EP | 750899 A2 | 1/1997 |
| WO | WO0031154 | 6/2000 |
| WO | WO0243689 A2 | 6/2002 |
| WO | WO2012050769 A1 | 4/2012 |

OTHER PUBLICATIONS

Co-Pending U.S. Appl. No. 61/562,455, filed Nov. 22, 2011; titled "Thickened Cosmetic Compositions".
Co-Pending U.S. Appl. No. 61/562,470, filed Nov. 22, 2011; titled "Glow and Sunless Tanning Color Enhancement by Polyhydroxy Quaternary Ammonium Salts".
Co-Pending U.S. Appl. No. 61/562,473, filed Nov. 22, 2011; titled "Sunscreen Composition With Polyhydroxy Quaternary Ammonium Salts".
Co-Pending U.S. Appl. No. 61/562,475, filed Nov. 22, 2011; titled "Foam Enhancement of Mild Surfactants with Polyhydroxy Quaternary Ammonium Salts".
Co-Pending U.S. Appl. No. 61/562,479, filed Nov. 22, 2011; titled "Preservative System Enhanced With Polyhydroxy Quaternary Ammonium Salts".
Co-Pending U.S. Appl. No. 61/562,481, filed Nov. 22, 2011; titled "Personal Care Compositions With Enhanced Fragrance Delivery Via Polyhydroxy Quaternary Ammonium Salts".
Co-Pending U.S. Appl. No. 61/562,482, filed Nov. 22, 2011; titled "Personal Care Compositions With Silicones and Polyhydroxy Quaternary Ammonium Salts".

* cited by examiner

*Primary Examiner* — Anand Desai
*Assistant Examiner* — Melissa Mercier
(74) *Attorney, Agent, or Firm* — Edward A. Squillante, Jr.

(57) ABSTRACT

A cosmetic composition is provided including a water-insoluble UV-A organic sunscreen agent having a $_{max}$ ranging from 330 to 380 nm, a UV-B organic sunscreen agent having a $_{max}$ ranging from 280 to 400 nm, and a photoprotective enhancing agent which is a polyhydroxy quaternary ammonium salt such as bis(dihydroxypropyl)dimethylammonium chloride, in a cosmetically acceptable carrier, and wherein the composition exhibits an SPF value which is 1 to 30 units higher than in the absence of the photoprotective enhancing agent.

12 Claims, No Drawings

SUNSCREEN COMPOSITION WITH POLYHYDROXY QUATERNARY AMMONIUM SALTS

BACKGROUND OF THE INVENTION

1. Field of the Invention

The invention concerns cosmetic compositions with enhanced photoprotection properties.

2. The Related Art

Many people dislike northern climates. There is a longing to bask in the warmth of the sun. Days at the beach find us in swimsuit attire. Many seek to turn their pale winter skin into a bronzed appearance. Others of naturally darker skin simply enjoy the refreshment of the seashore. Without protection from harmful ultraviolet radiation damage, these pleasures can turn into premature aging. Skin can lose elasticity and wrinkles appear in the premature aging process. Radiation can promote erythemal damage, can cause photo allergic reactions, and is implicated in skin cancers.

Protective measures are necessary. Lotions and creams formulated with sunscreens can shield against ultraviolet damaging radiation. The extent of protection varies widely.

Numerous ultraviolet photoprotective (sunscreen) agents are known. Nonetheless, only a small number are both commercially available and approved by regulatory authorities. A need exists to operate with known approved commercial sunscreen agents yet formulating them to achieve more than their expected level of photoprotection.

Representative of the art is U.S. Pat. No. 5,961,961 (Dobkowski et al.) reporting enhancement of the photoprotective effect by utilizing relatively large particle size titanium dioxide coupled with an organic sunscreen agent. Representative organic sunscreen agents include Benzophenone-3, octyl salicylate, octyl methoxycinnamate and 2-phenylbenzimidazole-5-sulphonic acid.

Although the aforementioned technology is useful, there is a need to achieve higher photoprotective efficacy for cosmetics.

SUMMARY OF THE INVENTION

A cosmetic composition is provided which includes:
(i) a water-insoluble UV-A organic sunscreen agent having a $\lambda_{max}$ ranging from 330 to 380 nm;
(ii) a UV-B organic sunscreen agent having a $\lambda_{max}$ ranging from 280 to 400 nm; and
(iii) a photoprotective enhancing agent having the structure (I)

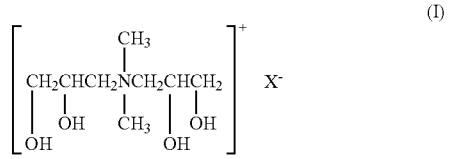

wherein X⁻ is selected from the group consisting of chloride, bromide, hydroxyl, sulphate, phosphate, methosulphate, carboxyl, citrate and tartrate;
(iv) a cosmetically acceptable carrier; and wherein the composition exhibits an SPF value which is 1 to 30 units higher than in the absence of the photoprotective enhancing agent.

DETAILED DESCRIPTION OF THE INVENTION

Now it has been found that photoprotection of sunscreen agents can be enhanced by combining a cocktail of two or more different types of the sunscreen agents with a photoprotective enhancing agent which is a polyhydroxy quaternary ammonium salt.

The photoprotective enhancing agent has the general structure as noted below:

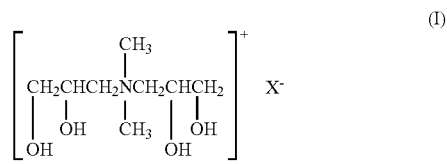

wherein X⁻ is selected from the group consisting of chloride, bromide, hydroxyl, sulphate, phosphate, methosulphate, carboxyl, citrate and tartrate. Most preferred as structure (I) is bis(dihydroxypropyl)dimethylammonium chloride.

Amounts of the polyhydroxy quaternary ammonium salt may range from about 0.05 to about 5%, or from about 0.1 to about 1%, or from about 1 to about 3%, and may also be from about 0.1 to about 0.5% by weight of the composition.

Cosmetic compositions of the present invention may include the following types of organic sunscreen agents. A first of these is a water-insoluble UV-A sunscreen agent having a $\lambda_{max}$ between 330 and 380 nm. Particularly the $\lambda_{max}$ will range from 340 to 360 nm, and optimally at 360 nm. In this category of sunscreen agent, the preferred materials are 4,4'-t-butyl methoxydibenzoylmethane known as Avobenzone (available as Parsol 1789®), 2-hydroxy-4-methoxybenzophenone known as Benzophenone-3 and as Oxybenzone, terephthalylidene dicamphor sulfonic acid (available as Mexoryl SX) and combinations thereof.

Amounts of the water-insoluble UV-A sunscreen agent may range from 1 to 8%, optimally from 2 to 3% by weight of the composition.

A second of the sunscreen agents is a water-insoluble or water soluble UV-B sunscreen agent having a $\lambda_{max}$ ranging between 280 and 400 nm. More particularly the $\lambda_{max}$ may range from 280 to 320 nm, and optimally at 305 nm.

A large variety of water-insoluble substances may be utilized as the UV-B sunscreen agent. Illustrative are 2-ethylhexyl p-methoxycinnamate, octyldimethyl p-aminobenzoic acid, digalloyltrioleate, ethyl 4-[bis(hydroxypropyl)]aminobenzoate, 2-ethylhexyl-2-cyano-3,3-diphenylacrylate, octylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, bis-ethylhexyloxyphenol methoxyphenol triazine, methylene bis-benzotriazolyl tetramethylbutylphenol, dimethicodiethylbenzal malonate, isoamyl methoxycinnamate, octyl triazone, and mixtures thereof.

Amounts of the water-insoluble UV-B sunscreen agent may range from 1 to 8%, preferably from 3 to 6%, and optimally about 5% by weight of the composition. Most preferred is 2-ethylhexyl p-methoxycinnamate.

Not only water-insoluble but also water soluble UV-B sunscreen agents separately or in combination may be utilized. An especially useful water-soluble sunscreen agent for this purpose is 2-phenylbenzimidazole-5-sulfonic acid and salt forms (available as Ensulizole®). Amounts of the water-soluble sunscreen agent may range from 1 to 8%, preferably from 2 to 3%, and optimally about 3% by weight of the composition.

When the water-soluble sunscreen agent is in salt form, advantageously the salt may be a metallic counter ion selected from sodium and potassium or an ammonium counter ion including triethanolammonium. Most preferred is a mixture of sodium and potassium counter ions, which when present may be found in a relative molar ratio sodium to potassium of 0.5:2 to 2:1, preferably 0.8:2 to 1.5:1, more preferably from 0.8:1 to 1:1.

Advantageously but not necessarily the amount of UV-A to UV-B sunscreen agent may range from about 1:5 to 1:1, more preferably from 1:4 to 2:5 by weight of the composition.

Increase in the SPF of the composition by the photoprotective enhancing agent over the same formula without the photoprotective enhancing agent should range from 1 to 30, preferably from 2 to 15, and optimally from 3 to 10 units.

Cosmetic compositions of the present invention may be but are not limited to cream or lotion form.

Also present in the compositions will be a cosmetically acceptable carrier. Carriers may be present in amounts ranging from about 5 to about 98%, preferably from about 20 to about 95%, optimally from about 40 to about 80% by weight of the cosmetic compositions. Water is the most common carrier for this invention. Oily carriers in the presence of water and an emulsifier will form emulsion systems as carriers. These systems may either be water-in-oil or oil-in-water emulsions. Besides water, suitable carrier classes include fatty acids, silicones, polyhydric alcohols, fatty alcohols, hydrocarbons, triglycerides and thickening powders.

Fatty acids may be selected from stearic acid, oleic acid, linoleic acid, linolinic acid, lauric acid, myristic acid, palmitic acid, behenic acid and mixtures thereof. Amounts may range from 1 to 50%, preferably from 8 to 30%, and optimally from 10 to 25% by weight of the composition.

Concentrations of the silicone may range from about 5% to about 60%, more preferably from about 5% to about 40%, by weight of the composition. These silicone fluids may be organic, silicone-containing or fluorine-containing, volatile or non-volatile, polar or non-polar.

Particularly preferred volatile silicone oils are cyclic volatile silicones wherein the repeating unit ranges from about 3 to about 5; and linear silicones wherein the repeating unit ranges from about 1 to about 7. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids, GE 7207 and 7158 (commercially available from G.E. Silicones) and SWS-03314 (commercially available from SWS Silicones Corp.

Hydrocarbons may be useful as cosmetically acceptable carriers for compositions of this invention. They may include mineral oil, petrolatum and polyalpha-olefins. Examples of preferred volatile hydrocarbons include polydecanes such as isododecane and isodecane (e.g., Permethyl-99A which is available from Presperse Inc.) and the C7-C8 through C12-C15 isoparaffins (such as the Isopar Series available from Exxon Chemicals).

Polyhydric alcohols may serve as carriers. Illustrative of this group are propylyene glycol, dipropylene glycol, polypropylene glycol, polyethylene glycol, sorbitol, hydroxypropyl sorbitol, hexylene glycol, 1,3-butylene glycol, isoprene glycol, ethoxylated glycerol, propoxylated glycerol and mixtures thereof. Most preferred is glycerol known also as glycerin.

Fatty alcohols may also be useful carriers. The term "fatty" refers to carbon chain lengths ranging from 10 to 30 carbon atoms. Illustrative of this category are lauryl alcohol, cetyl alcohol, stearyl alcohol, isostearyl alcohol and combinations thereof.

Triglycerides are another group of materials useful as carriers. Illustrative but not limiting are sunflower seed oil, cotton oil, canola oil, soybean oil, castor oil, borage oil, olive oil, shea butter, jojoba oil and mixtures thereof. Mono- and diglycerides may also be useful. Illustrative of these categories are glyceryl monostearate and glyceryl distearate.

The carriers can comprise one or more thickening agents, preferably from about 0.05% to about 10%, more preferably from about 0.1% to about 5%, and even more preferably from about 0.25% to about 4%, by weight for the composition.

Cosmetic compositions of the present invention may contain a variety of optional components to enhance physical properties and performance.

The optional components, when incorporated into the cosmetic compositions, should be suitable for use in contact with human keratinous tissue without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these classes include: abrasives, absorbents, aesthetic components such as fragrances, pigments, colorings/colorants, essential oils, skin sensates, astringents, etc. (e.g. clove oil, menthol, camphor, eucalyptus oil, eugenol, menthyl lactate, witch hazel distillate), anti-acne agents, anti-caking agents, antifoaming agents, antimicrobial agents, antioxidants, biological additives, buffering agents, bulking agents, chelating agents, chemical additives, colorants, cosmetic astringents, cosmetic biocides, denaturants, drug astringents, external analgesics, film forming polymers, opacifying agents, pH adjusters, propellants, reducing agents, sequestrants, skin bleaching and lightening agents, skin conditioning agents, skin soothing and/or healing agents and derivatives, skin treating agents, thickeners, and vitamins and derivatives thereof.

A safe and effective amount of an anti-oxidant/radical scavenger may be added in amounts from about 0.01% to about 10%, more preferably from about 0.1% to about 5% by weight of the composition.

Anti-oxidants/radical scavengers may be employed such as ascorbic acid (vitamin C) and its salts, ascorbyl esters of fatty acids, ascorbic acid derivatives (e.g. magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolor®), amines (e.g. N,N-diethylhydroxylamine, amino-guanidine), nordihydroguaiaretic acid, bioflavonoids, amino acids, cassia plant and extracts, silymarin, tea extracts, and grape skin/seed extracts. Preferred anti-oxidants/radical scavengers are selected from esters of tocopherol, more preferably tocopherol acetate.

The cosmetic compositions may optionally comprise a flavonoid compound. Flavonoids are disclosed in U.S. Pat. Nos. 5,686,082 and 5,686,367 herein incorporated by reference. Examples of flavonoids particularly suitable flavones, isoflavones, coumarins, chromones, discoumarols, chromanones, chromanols, isomers (e.g. cis/trans isomers) thereof, and mixtures thereof.

Preferred for use are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy), and mixtures thereof. Flavonoid compounds useful herein are commercially available from a number of sources, e.g., Indofine Chemical Company, Inc., Stearloids, Inc., and Aldrich Chemical Company, Inc. The herein described flavonoid compounds are preferably present in from about 0.01% to about 20%, more preferably from about 0.1% to about 10%, and even more preferably from about 0.5% to about 5% by weight.

Anti-inflammatory agents useful herein include allantoin and compounds of the Licorice (the plant genus/species *Glycyrrhiza glabra*) family, including glycyrrhetic acid, glycyrrhizic acid, and derivatives thereof (e.g. salts and esters).

The compositions may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include niacinamide, kojic acid, arbutin, tranexamic acid, placental extract, ascorbic acid and derivatives thereof (e.g. magnesium ascorbyl phosphate, sodium ascorbyl phosphate, ascorbyl glucoside, and ascorbyl tetraisopalmitates). Other skin lightening materials suitable for use herein include Actiwhite® (Cognis), Emblica® (Rona), Azeloglicina (Sinerga) and extracts (e.g. mulberry extract).

The compositions may comprise an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and even more preferably from about 0.05% to about 2% by weight of the composition.

Preferred examples of these actives include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cystein, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, climbazole, miconazole, ketoconazole, neocycin sulfate, and mixtures thereof.

The compositions may comprise a conditioning agent selected from the group consisting of humectants, moisturizers, or skin conditioners. A variety of these materials can be employed and each can be present at a level of from about 0.01% to about 40%, more preferably from about 0.1% to about 30%, and even more preferably from about 0.5% to about 15% by weight of the composition. These materials include, but are not limited to, guanidine; urea; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy compounds such as sorbitol, mannitol, glycerol, hexanetriol, butanetriol, propylene glycol, butylene glycol and hexylene glycol; polyethylene glycols; sugars and starch derivatives (e.g. alkoxylated glucose, fructose, sucrose, trehalose); hyaluronic acid; lactamide monoethanolamine; acetamide monoethanolamine; sucrose polyester; petrolatum; and mixtures thereof.

The cosmetic compositions include but are not limited to lotions, milks, mousses, serums, sprays, aerosols, foams, sticks, pencils, gels, creams and ointments. The compositions may also be applied via a woven or nonwoven synthetic and/or natural fibered textile (wipe or towelette).

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

The following examples will more fully illustrate the embodiments of this invention. All parts, percentages and proportions referred to herein and in the appended claims are by weight unless otherwise illustrated.

EXAMPLES 1-8

A series of compositions are outlined in Table I which are illustrative of the present invention.

TABLE I

| Component | Sample No. (Weight %) | | | | | | | |
|---|---|---|---|---|---|---|---|---|
| | 1 | 2 | 3 | 4 | 5 | 6 | 7 | 8 |
| Stearic Acid | 15.0 | 15.0 | 5.0 | 10.0 | 10.0 | 8.0 | 8.0 | 8.0 |
| Glycol Stearate | 8.0 | 8.0 | 5.0 | 5.0 | 8.0 | 8.0 | 8.0 | 8.0 |
| Glycerol Monostearate | 2.5 | 4.5 | 1.5 | 1.5 | 2.5 | 2.5 | 2.5 | 2.5 |
| Cetyl Alcohol | 1.5 | 0.5 | 0.5 | 1.0 | 1.0 | 1.0 | 1.0 | 1.0 |
| PEG-100 Stearate | 1.5 | 2.5 | 1.5 | 2.5 | 2.5 | 2.5 | 1.5 | 1.5 |
| Potassium Stearate | 1.0 | 1.5 | 0.8 | 0.8 | 3.0 | 1.5 | 1.5 | 1.1 |
| Avobenzone | 2.0 | 2.0 | 3.0 | 3.0 | 2.0 | 2.0 | 3.0 | 3.0 |
| 2-Ethylhexylmethoxycinnamate | 5.0 | 5.0 | 5.0 | 5.0 | 5.0 | 5.0 | 5.0 | 5.0 |
| 2-Phenylbenzimidazole-5-sulfonate salt | 1.2 | — | — | — | 1.2 | 1.2 | 1.5 | 1.0 |
| bis(dihydroxypropyl) dimethylammonium chloride | 1.0 | 2.5 | 4.0 | 0.8 | 0.5 | 3.0 | 0.1 | 1.5 |
| Glycerin | 5.0 | 5.0 | 5.0 | 5.0 | 5.0 | 5.0 | 5.0 | 5.0 |
| Silicone Oil | 0.5 | 0.5 | 0.5 | 0.5 | 0.5 | 0.5 | 0.5 | 0.5 |
| Isopropyl Myristate | 0.75 | 0.75 | 0.75 | 0.75 | 0.75 | 0.75 | 0.75 | 0.75 |
| Methyl Paraben | 0.15 | 0.15 | 0.15 | 0.15 | 0.15 | 0.15 | 0.15 | 0.15 |

TABLE I-continued

| | Sample No. (Weight %) | | | | | | | |
|---|---|---|---|---|---|---|---|---|
| Component | 1 | 2 | 3 | 4 | 5 | 6 | 7 | 8 |
| Propyl Paraben | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 |

EXAMPLE 9

Photoprotective effects were evaluated on a model system wherein the lamellar oil phase of an aqueous emulsion had the formulas outlined in Table II.

TABLE II

| | Formula (Wt. % Active) | | | | | | |
|---|---|---|---|---|---|---|---|
| Component | A | B | C | D | E | F | G |
| Stearic Acid | 1.58 | 1.58 | 1.58 | 1.58 | 1.58 | 1.58 | 1.58 |
| Glyceryl Monostearate | 0.81 | 0.81 | 0.81 | 0.81 | 0.81 | 0.81 | 0.81 |
| Cetyl Alcohol | 0.47 | 0.47 | 0.47 | 0.47 | 0.47 | 0.47 | 0.47 |
| PEG-100 Stearate | 1.50 | 1.50 | 1.50 | 1.50 | 1.50 | 1.50 | 1.50 |
| Avobenzone | 1.50 | 1.50 | 1.50 | 1.50 | 1.50 | 1.50 | — |
| 2-Ethylhexylmethoxycinnamate | 3.00 | 3.00 | 3.00 | — | — | — | — |
| 2-Phenylbenzimidazole-5-sulfonic salt (in aqueous phase) | — | — | — | 3.00 | 3.00 | 3.00 | — |
| Bis(dihydroxypropyl)-dimethylammonium chloride | — | 2.00 | — | — | 2.00 | — | 2.00 |
| Dihydroxypropyl-trimethylammonium chloride | — | — | 2.00 | — | — | 2.00 | — |

Procedure

SPF Measurements

Sun protection factor (SPF) was measured in vitro using an Optometrics SPF 290 instrument. The test procedure required calibration of the monochrometer and sample stage of the Optometrics SPF 290 instrument. Thereafter the instrument was calibrated with a blank sample quartz plate (10 cm×10 cm and 3 mm thickness). Calibration zeros the UV detector. Formulas were applied and spread uniformly onto a plate to leave a film of 2 mg/cm². The film was left to dry for 30 minutes. Subsequently an SPF reading was taken on the dried film using three measurements on different parts of the coated quartz plate and recording an average value. For the present experiments the wavelength is the peak maximum at 305 to 360 nm.

Results

The SPF in vitro results on the formulas detailed under Table II are recorded in Table III below.

TABLE III

| Formula | SPF (2 mg/cm²) |
|---|---|
| A | 17 |
| B | 23 |
| C | 20 |
| D | 10 |
| E | 18 |
| F | 11 |
| G | 2.4 |

Evident from the results is that the presence of bis(dihydroxypropyl)dimethylammonium chloride enhanced photoprotection. Compare Formula A with B and D with E which show an increase of from 6 to 8 units of SPF in the presence of the photoprotective enhancing agent. A compound similar to the enhancer of this invention, dihydroxypropyltrimethylammonium chloride, was much less effective at improving the SPF. Compare results of Formula B versus C and Formula E versus F.

EXAMPLE 10

Synthesis of Bis-(2.3-dihydroxypropyl)dimethylammonium Chloride

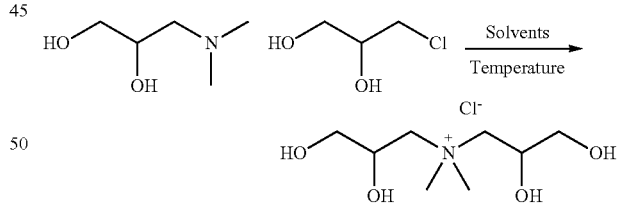

General Procedure: Dimethylaminopropanediol (20 g, 0.168 moles) and 3-Chloropropane-1,2-diol (18.5 g, 0.168 moles) were stirred in ethanol (40 mL) at 70° C. until the reaction is complete. The reaction was monitored by LCMS. Upon completion, the reaction was allowed to cool and the solution was poured to a mixture of acetone:methyl-tert-butyl ether (2:1, 300 mL) to oil out the product. The Supernatant was decanted and product was washed with a mixture of acetone/methyl-tert-butyl ether (2×300 mL). The oil obtained was dried over high vacuum followed by freeze drying to obtain colorless oil/semisolid (>90% yield). The pure product was characterized using $^1$H NMR, $^{13}$C NMR, and MS. Details on characterization as follows.

Analytical Instrumentation Used:

LC MS: The MS of the compound was recorded using a Micromass Quattro Ultima LCMS system with Mass Lynx 4.1 software equipped with Agilent 1100 LC system. A solution of 50 ppm was infused in the LCMS system using 50:50 Methanol: 5 mM HCOOH as the mobile phase and ESI positive source.

NMR: A sample (144 mg) was dissolved in $D_2O$ (650 mL) and analyzed by $^1H$ and $^{13}C$ NMR using a Varian Eft-60 NMR Spectrometer (60 MHz) and the data processed using Nuts Pro (2D Professional version, Acorn NMR).

Characterization of Bis-(2.3-dihydroxypropyl)dimethylammonium Chloride:

$^1H$ NMR ($D_2O$, 60 MHz) δ 3.22 (s, 6H, $CH_3$), 3.48 (s, 4H, $CH_2$), 3.57 (s, 4H, $CH_2$), 4.2 (bm, 2H, —CH), $^{13}C$ NMR ($D_2O$) δ 52.72 ($CH_{3's}$), 63.55 (—$CH_2$), 65.97 (—CH), 67.24 (—$CH_{2's}$) LCMS (M-Cl) 194.25 (calcd), 194.22 (observed).

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

What is claimed is:

1. A cosmetic composition comprising:
   (i) a water-insoluble UV-A organic sunscreen agent having a $\lambda_{max}$ ranging from 330 to 380 nm;
   (ii) a UV-B organic sunscreen agent having a $\lambda_{max}$ ranging from 280 to 400 nm; and
   (iii) a photoprotective enhancing agent having the structure (I)

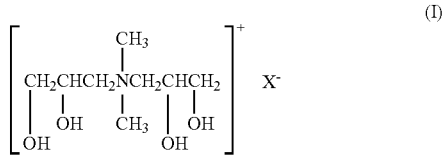

wherein $X^-$ is selected from the group consisting of chloride, bromide, hydroxyl, sulphate, phosphate, methosulphate, carboxyl, citrate and tartrate;

(iv) a cosmetically acceptable carrier; and wherein the composition exhibits an SPF value which is 1 to 30 units higher than in the absence of the photoprotective enhancing agent.

2. The composition according to claim 1 wherein the water-insoluble UV-A organic sunscreen agent is Avobenzone or Benzophenone-3.

3. The composition according to claim 1 wherein the UV-B organic sunscreen agent is 2-ethylhexylmethoxycinnamate.

4. The composition according to claim 1 wherein the UV-B sunscreen agent is 2-phenylbenzimidizole-5-sulfonic acid or salt thereof.

5. The composition according to claim 1 wherein the photoprotective enhancing agent is present in an amount from about 0.05 to about 5% by weight of the composition.

6. The composition according to claim 1 wherein the UV-A organic sunscreen agent is present in an amount from 1 to 8% by weight of the composition.

7. The composition according to claim 1 wherein the UV-B organic sunscreen agent is present in an amount from 1 to 8% by weight of the composition.

8. The composition according to claim 1 wherein the photoprotective enhancing agent is present in an amount from about 1 to about 3% by weight of the composition.

9. The composition according to claim 1 wherein the polyhydroxy quaternary ammonium salt is bis(dihydroxypropyl) dimethylammonium chloride.

10. The composition according to claim 1 wherein the composition is a lotion, ointment, cream, gel or stick.

11. The composition according to claim 1 wherein the composition is a spray, aerosol, pencil, serum or mousse.

12. The composition according to claim 1 wherein the composition further comprises niacinamide, kojic acid, ascorbic acid, climbozole, menthol, eugenol or a mixture thereof.

* * * * *